United States Patent [19]
Fucci et al.

[11] Patent Number: 5,697,950
[45] Date of Patent: Dec. 16, 1997

[54] PRE-LOADED SUTURE ANCHOR

[75] Inventors: Joseph Fucci; Bennie W. Gladdish, Jr., both of Palm Harbor, Fla.

[73] Assignee: Linvatec Corporation, Largo, Fla.

[21] Appl. No.: 597,792

[22] Filed: Feb. 7, 1996

[51] Int. Cl.$^6$ .................................................. A61B 17/04
[52] U.S. Cl. .......................... 606/232; 606/148; 606/139
[58] Field of Search ................................. 606/232, 145, 606/148, 75, 73, 104, 139

[56] References Cited

U.S. PATENT DOCUMENTS

| | | |
|---|---|---|
| 4,244,370 | 1/1981 | Furlow et al. |
| 4,409,974 | 10/1983 | Freedland. |
| 4,632,100 | 12/1986 | Somers et al. |
| 4,738,255 | 4/1988 | Goble et al. |
| 4,741,330 | 5/1988 | Hayhurst. |
| 4,898,156 | 2/1990 | Gatturna et al. |
| 4,968,315 | 11/1990 | Gatturna. |
| 4,976,712 | 12/1990 | Vandersilk. |
| 4,989,764 | 2/1991 | Hoffman et al. |
| 5,034,012 | 7/1991 | Frigg. |
| 5,037,422 | 8/1991 | Hayhurst et al. |
| 5,041,129 | 8/1991 | Hayhurst et al. |
| 5,084,063 | 1/1992 | Korthoff .................. 606/226 |
| 5,100,417 | 3/1992 | Cerier et al. |
| 5,102,421 | 4/1992 | Anspach, Jr. |
| 5,139,520 | 8/1992 | Rosenberg. |
| 5,141,520 | 8/1992 | Goble et al. |
| 5,156,616 | 10/1992 | Meadows et al. |
| 5,176,682 | 1/1993 | Chow. |
| 5,224,946 | 7/1993 | Hayhurst et al. |
| 5,258,016 | 11/1993 | DiPoto et al. |
| 5,268,001 | 12/1993 | Nicholson et al. |
| 5,368,595 | 11/1994 | Lewis. |
| 5,382,257 | 1/1995 | Lewis et al. |
| 5,411,506 | 5/1995 | Goble et al. |
| 5,411,523 | 5/1995 | Goble. |
| 5,423,860 | 6/1995 | Lizardi et al. |
| 5,534,011 | 7/1996 | Greene, Jr. et al. |
| 5,578,057 | 11/1996 | Wenstrom, Jr. .......... 606/232 |
| 5,584,860 | 12/1996 | Goble et al. ............. 606/232 |

OTHER PUBLICATIONS

Article Entitled "Mini-Statak Soft Tissue Attachment Device", Fracture Management, Zimmer, Feb. 1992, 4 Pages.
Article Entitled "Statak Soft Tissue Attachment Device", Fracture Management, Zimmer, Rev. Nov. 1989, 4 pages.
Product Information, "Rotator Cuff Repair With a New Twist" Linvatec, 1993, 2 pages.

*Primary Examiner*—Michael Buiz
*Assistant Examiner*—Tina T. D. Pham
*Attorney, Agent, or Firm*—Gene Warzecha

[57] ABSTRACT

A method and apparatus for facilitating use of a threaded suture anchor in combination with a reusable cannulated anchor driver. The device enables a suture anchor to be preassembled with a suture so that a user need not assemble a suture anchor with suture immediately prior to use. The preassembled anchor/suture is provided with a suture stiffening or support member by which the free ends of the suture may be easily threaded into the axial bore of a cannulated driver. The support member may comprise a length of shrinkable tubing frictionally engaging at least a portion of the free ends of the suture extending from the anchor. In another embodiment, the support means may comprise an elongated non-shrinkable material such as a rod attached to the suture and enabling the anchor/suture/rod assembly to be threaded into a cannulated driver simply by the force of gravity acting upon the rod.

16 Claims, 6 Drawing Sheets

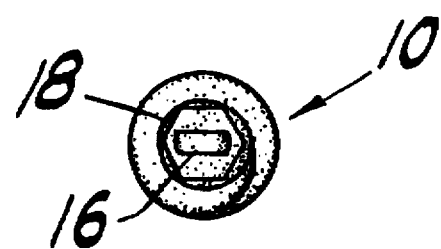
Fig. 3
Prior Art
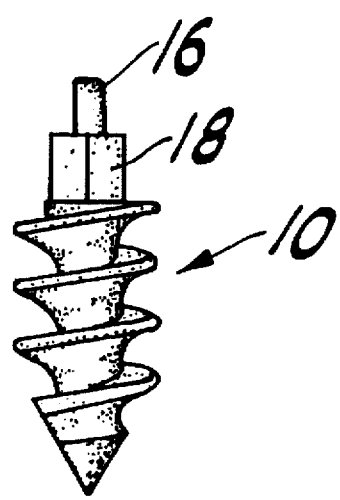
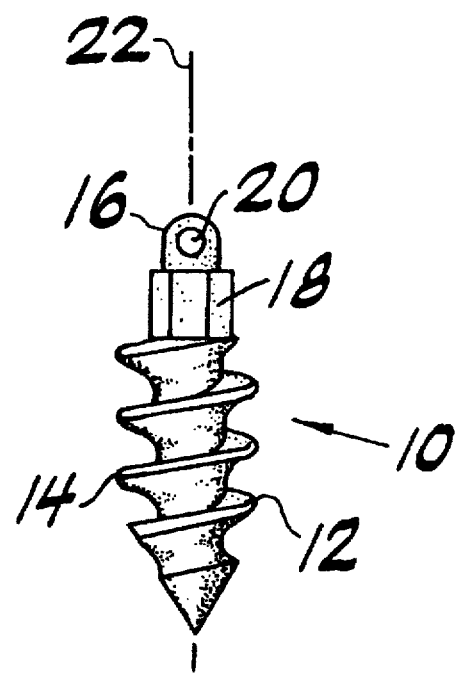
Fig. 2
Prior Art
Fig. 1
Prior Art

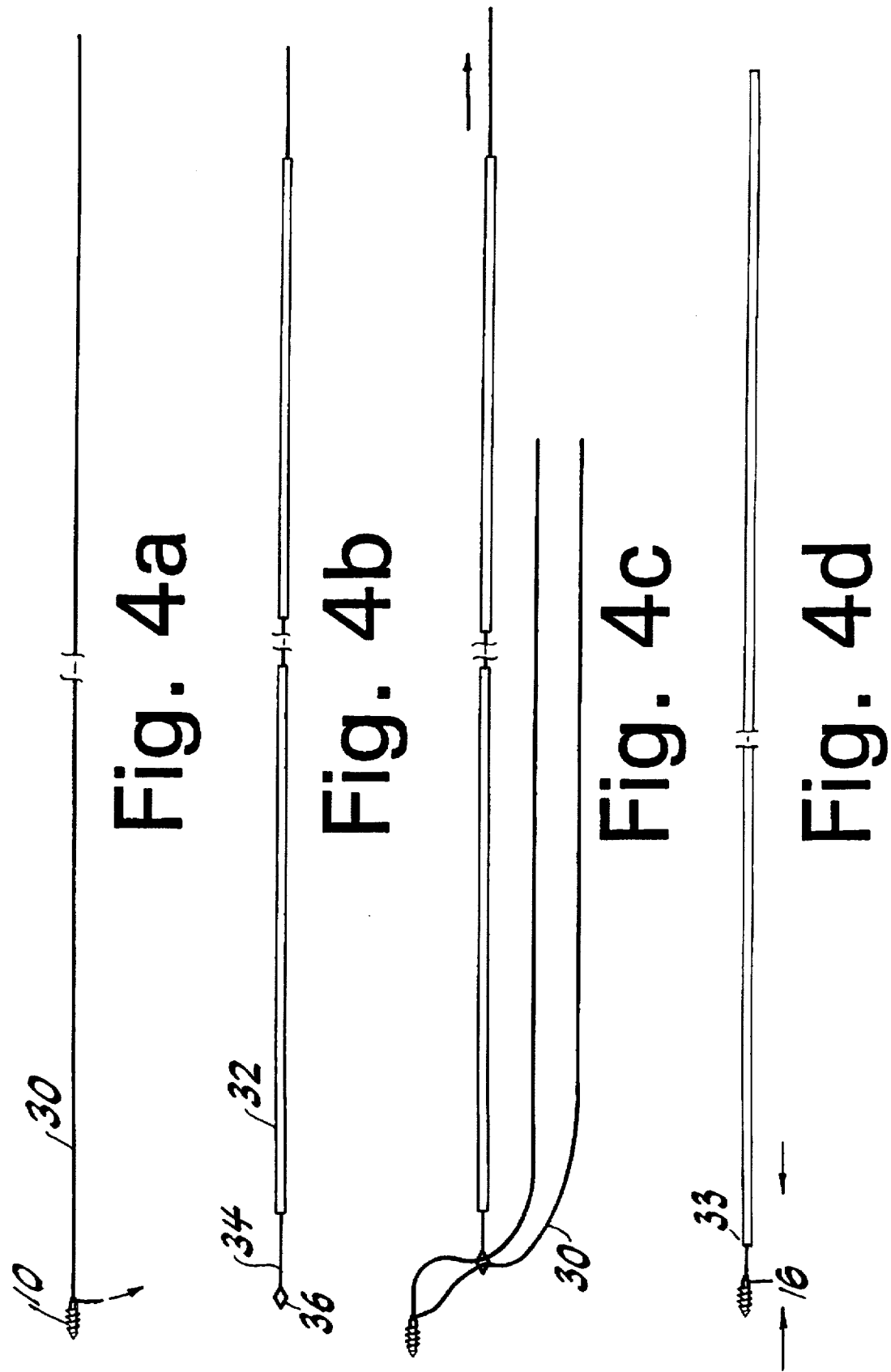

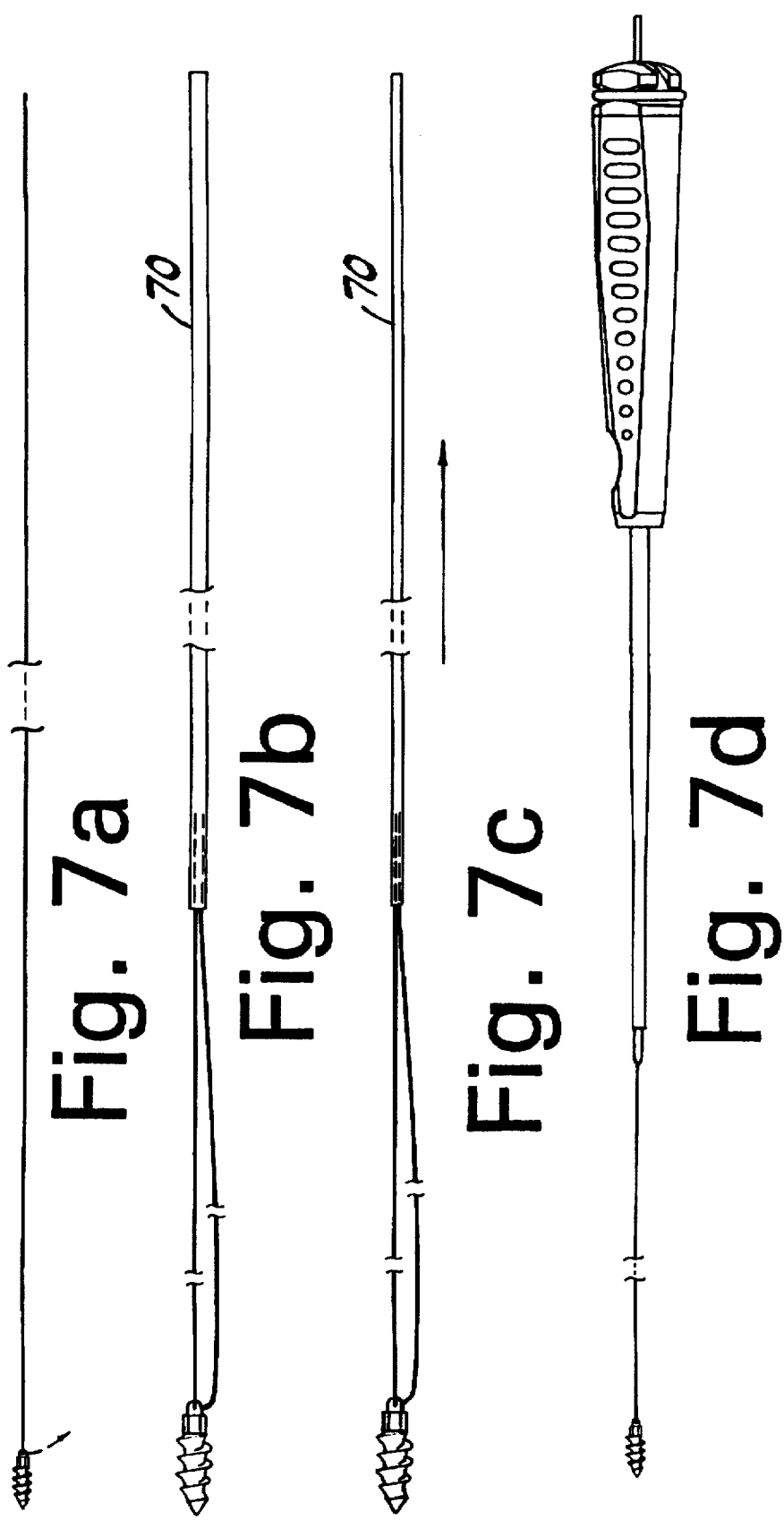

PRE-LOADED SUTURE ANCHOR

BACKGROUND OF THE INVENTION

1. Field of the Invention

The invention relates generally to suture anchors for attaching soft tissue to bone. More particularly, the invention relates to a method and apparatus for producing a pre-loaded suture anchor assembly to facilitate attachment of a threaded suture anchor to a suture anchor driver for attaching the suture anchor at a selected work site.

2. Description of the Prior Art

In the course of certain surgical procedures, soft tissue is secured to a selected bone surface either directly, via some type of implant, or indirectly via an implant (i.e. an anchor) to which suture is attached, the suture then being tied to the soft tissue to hold it in place. Anchors may be used to attach soft tissue such as ligaments, tendons, muscles, etc. to a surface from which the soft tissue has become detached and may also be used to secure soft tissue to supplementary attachment sites for reinforcement. For example, in urological applications anchors may be used in bladder neck suspensions to attach a portion of the bladder to an adjacent bone surface. Such soft tissue attachment may be done during either open or closed surgical procedures, the latter being generally referred to as arthroscopic or endoscopic surgery. The terms "arthroscopic" and "endoscopic" may be used interchangeably herein and are intended to encompass arthroscopic, endoscopic, laparoscopic, hysteroscopic or any other similar surgical procedures performed with elongated instruments inserted through small openings in the body.

The prior art includes numerous types of suture anchors adapted to be secured in the bone, sometimes directly in one step and sometimes in pre-drilled holes or tunnels. The term "suture anchor" is used broadly and will be understood to refer to devices having a similar structure even if material other than suture is connected to the device. These devices generally comprise an anchor body designed to be embedded in the bone at a selected work site and a length of suture or other elongated structure extending from the body. The suture provides a means to tie the soft tissue adjacent the bone into which the anchor body has been embedded. While suture is sometimes tied to a portion of the anchor body, often the suture is threaded (i.e. pre-loaded) through an eyelet or other aperture in the anchor body so the suture may slide within the eyelet to facilitate subsequent knot tying steps. Alternatively, the suture may be non-slidably attached to have one or two fixed-length ends extending from the anchor body. Some prior art suture anchors are elongated and have annular ribs or radially extending barbs and are required to be pushed or hammered directly into bone or into a pre-formed bone tunnel (exemplified by U.S. Pat. Nos. 5,102,421 (Anspach, Jr.); 5,141,520 (Goble et al.); 5,100,417 (Cerier et al.); 5,224,946 (Hayhurst et al.) and 5,261,914 (Warren)). Other suture anchors are threaded in order to be screwed into bone as exemplified by U.S. Pat. Nos. 5,156,616 (Meadows et al.) and 4,632,100 (Somers et al.).

Devices used to insert suture anchors into bone surfaces are known as drivers and provide an interface between the actual implant and the surgeon performing the procedure. While this interface is most important in endoscopic surgical procedures because of the limited accessibility of the surgical site, prior art endoscopic procedures generally utilize devices and methods designed for open surgical procedures. All known procedures used to insert suture anchors endoscopically rely on elongated extensions which pass through the portals or cannulas used in the procedures. Similar elongated extensions are also used in open procedures. With respect to non-threaded or non-turnable suture anchors, these extensions merely are required to transmit longitudinal forces from the proximal end to the distal end where the suture anchor is situated. With respect to turnable or threaded suture anchors, the inserting device must be elongated as well as strong enough to transmit sufficient torque from the proximal end to the distal tip to turn the anchor.

Suture anchors are often shipped to the customers with the suture already joined to the anchor body and with the body in turn attached to the driver, i.e. pre-loaded. The driver must, therefore, accommodate suture while it is turning. For example, U.S. Pat. Nos. 5,411,506 (Goble et al.) and 5,411,523 (Goble) disclose a prior art suture anchor/driver assembly showing an anchor body preattached to sutures and held at the distal end of a cannulated driver. During arthroscopic or endoscopic procedures an elongated anchor/driver assembly enables a surgeon to manipulate the anchor within a portion of the body accessible only through a portal or other opening in the body. The suture anchor is provided with some means by which it may be attached and held to the distal end of the elongated driver while the proximal end is driven by the user.

It is also known to provide a user with an unthreaded suture anchor body which must then be threaded and attached to a driver. For example, U.S. Pat. No. 5,423,860 (Lizardi et al.) shows a device which facilitates loading a suture anchor into a non-cannulated driver. This device is a protective carrier in the form of a sleeve body which almost completely surrounds a suture anchor body having an aperture through its tip. The suture attached to the suture anchor is not retained by the protective carrier. The purpose of the protective carrier is to facilitate holding of the anchor as it is manipulated in order to thread a suture onto the anchor prior to assembling the anchor to the driver.

Suture anchor drivers may be either disposable or reusable. A significant factor in determining whether a particular driver is reusable is the ease with which a suture anchor may be threaded with suture and then threaded through or attached to the driver to produce a pre-loaded anchor/driver assembly. The small sizes of the eyelets or other apertures make threading suture a time consuming process at best, especially in an operating room setting. Additionally, such threading through either an eyelet of the anchor or through the axial bore of a driver requires the use of elongated needle threaders and thereby adds to the complexity of equipment required for given surgical procedures. The aforementioned Lizardi et al. patent shows one type of reusable driver system utilizing a non-cannulated driver. The drivers in the aforementioned Goble patents are, however, cannulated and, therefore, not amenable to being easily loaded by a user.

Prior art suture anchors are supplied to the customers pre-loaded as suture anchor/driver assemblies which utilize disposable cannulated drivers primarily because it is very difficult for a user to reuse the driver by attaching a suture to a new anchor body and then attaching the threaded anchor body to the driver. Attachment to a cannulated driver requires threading a flexible suture through a long, axial bore of the driver.

It is accordingly an object of this invention to provide a method and device for facilitating the attachment of a suture anchor to a driver.

It is also an object of this invention to provide a method and device for utilizing a pre-loaded suture anchor which may be easily assembled with a cannulated driver without use of other tools.

It is an additional object of this invention to provide a method and device for enabling a user (such as a surgeon or other health care worker) to easily load (i.e. thread) a pre-loaded suture anchor into a reusable cannulated driver.

SUMMARY OF THE INVENTION

These and other objects of the invention are achieved by the preferred embodiment disclosed herein which is a pre-loaded suture anchor assembly comprising: an anchor body having a suture receiving means for receiving suture; a suture having predetermined length and having a first end and a second end, said suture received in said suture receiving means and extending therefrom; a suture retaining means secured to said first and second ends of said suture for holding said ends of said suture. The suture retaining means may be a heat-shrinkable tube or an elongated rod swaged to the end of the suture.

The invention also resides in a method of producing a pre-loaded suture anchor assembly for attachment to a suture anchor driver comprising the steps of: providing a suture anchor having a suture receiving means for receiving suture; providing a predetermined length of suture; engaging a predetermined length of suture with said suture receiving means so that at least one end of said suture extends from said suture anchor; providing a predetermined length of suture-supporting means for decreasing the lateral flexibility of an end portion of said suture to enable said suture to be engaged endwise with said driver; placing said at least one end of said suture into one end of said suture-supporting means; activating said suture-supporting means in order to cause it to frictionally engage said suture.

BRIEF DESCRIPTION OF THE DRAWINGS

FIG. 1 is a side elevational view of a prior art suture anchor.

FIG. 2 is a left side view of FIG. 1.

FIG. 3 is a top plan view of FIG. 1.

FIGS. 4a through 4f are sequential views of the steps involved in forming one embodiment of the invention.

FIGS. 7a through 7d show the steps involved in producing an alternative embodiment of the invention.

DESCRIPTION OF THE PREFERRED EMBODIMENT

Figure 4E:
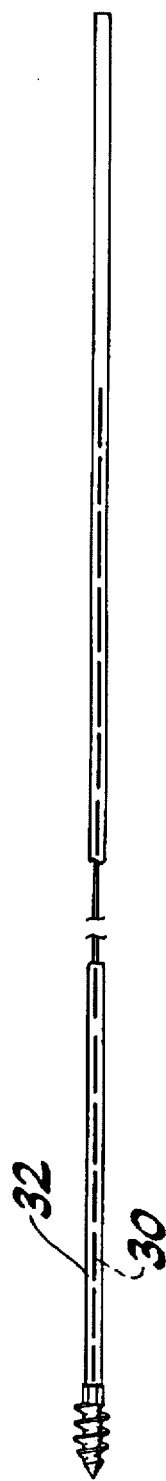

The method and apparatus of the present invention are best understood by reference to the Figures. While the invention is suitable for use with a variety of suture anchors, the preferred embodiment of the invention disclosed herein is explained in the context of a prior art threaded suture anchor 10 shown in FIGS. 1 through 3 and sold under the trademark REVO by Linvatec Corporation, 11311 Concept Boulevard, Largo, Fla. 34643. Suture anchor 10 comprises an anchor body 12 having a threaded distal portion 14, an apertured, proximal suture receiving portion 16 and an intermediate, hexagonally profiled drive portion 18. Suture receiving portion 16 has an eyelet 20 with an axis transverse to axis 22 of anchor body 12, the eyelet having a diameter sufficient to accommodate a selected suture.

Figure 4F:

As shown in FIG. 4a, eyelet 20 of suture anchor 10 is threaded (by means not shown) with a predetermined length of suture 30 which is long enough to be suitable for the procedure for which the suture anchor is intended. Suture 30 is threaded through the eyelet and folded back upon itself to have both ends placed side by side and to produce two equal-length suture portions extending from eyelet 20. (It is noted that some anchors and situations may utilize only a single suture portion extending from the anchor.) An elongated suture threader 34 is inserted axially into and through a length of shrinkable polymeric tubing 32 (FIG. 4b) and both ends of suture 30 are passed through the pliable loop 36 at the distal end of threader 34 (FIG. 4c). Pulling threader 34 out of tubing 32 causes suture 30 to extend axially through tubing 32 (FIG. 4d), the distal end 33 of the tubing is then, in this embodiment, positioned over suture retaining portion 16 and/or the hexagonal drive portion 18 (FIG. 4e). Other methods of threading the suture through the tubing may also be utilized. As will be explained further below, it should be noted that suture 30 need not extend entirely through tubing 32 and that the tubing may extend beyond the suture. Tubing 32 must be a material which has an initial large internal diameter to easily receive the suture. Applying heat or some other stimulus to tubing 32 (by means not shown) causes it to shrink around suture 30 to a smaller diameter and frictionally engage both the suture and the eyelet portion as shown in FIG. 4f, or just the suture alone.

Figure 6:
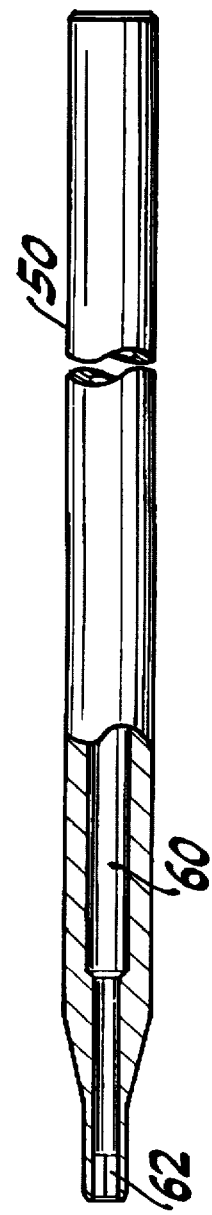
FIG. 6 is an exploded view of the distal tip of the driver of FIG. 5, partially in cross-section.
Figure 5:
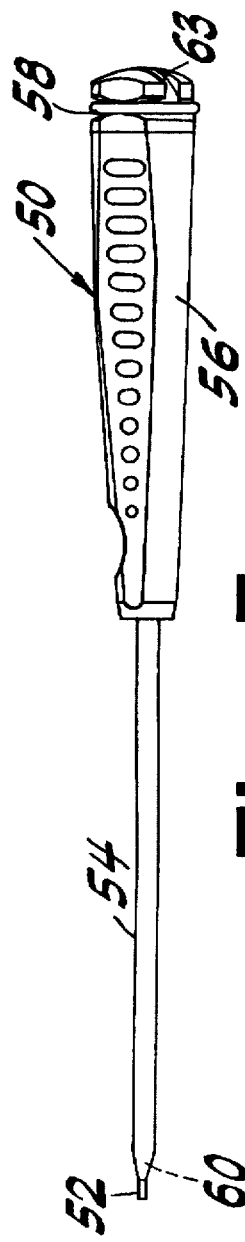
FIG. 5 is a side elevational view of a cannulated driver used to insert a suture anchor at a surgical site.

As shown in FIGS. 5 and 6, reusable suture anchor driver 50 has a distal tip 52, an elongated body 54, a handle 56, a suture retaining O-ring 58 and is cannulated throughout by axial bore 60. The distal end of bore 60 communicates with interior channel 63 in the hollow, hexagonal driver tip adapted to receive suture and drive portion 18 of the suture anchor. Driver 50 is known and often used with a threaded suture anchor such as anchor 10. However, prior to this invention, such use required the user to laboriously thread suture through the anchor body and then through the bore 60 of the driver. After this was done, the suture extending from the proximal end of bore 60 was held in place by lying in one of three radially extending grooves 62 (between bore 60 and O-ring 58) and being wrapped circumferentially around the driver handle adjacent O-ring 58. As will be understood below, the invention facilitates the assembly of the anchor with the driver. The proximal end of tubing 32 must, after shrinking, be sufficiently small in diameter to enable it to pass through channel 62.

In one preferred embodiment of this invention the maximum dimension of suture retaining portion 16 is 0.064 inches while the maximum dimension of the hexagonal drive portion 18 across the flats is 0.077 inches. It has been found that shrinkable tubing having an outside diameter of 0.072 inches before heating and an outside diameter of 0.065 inches after heating is suitable for use with such an anchor. While numerous types of heat skrinkable tubing may be used, the shrink tubing may be, for example, fluorinated ethylenepropylene having a minimum expanded ID of 0.060 and a maximum recovered ID of 0.049. With respect to a second example, a smaller, Mini-REVO suture anchor having a maximum eyelet dimension of 0.055 inches and a maximum hexagonal dimension across the flats of 0.0557 may also be used. For this embodiment a shrinkable tube having an outside dimension of 0.062 inches before heating and 0.054 inches after heating is suitable, this shrink tubing having a minimum expanded ID of 0.054 inches and a maximum recovered ID of 0.044 inches. Both REVO and Mini-REVO suture anchors are usable with number 0 braided polyester suture (3.55 mm metric) having an outside diameter of 0.35 mm min/0.399 mm max and, since the shrinkage of the tubing is effective over a wide range, the system is also usable with a number 1 or 2 braided polyester suture (4 mm, 5 mm) having an outside diameter of 0.40 mm min/0.499 mm max or 0.50 mm min/0.599 mm max, respectively. Obviously, threading the larger sutures through the tubing prior to shrinking will be more difficult although the resilience of the tubing permits considerable variation in sizes.

The embodiment of FIG. 4 is used by simply pushing the free end of the anchor/suture/tubing assembly into the distal tip of channel 62 until it emerges from the proximal end of the driver bore. The assembly may then be pulled the rest of the way until the anchor is seated in channel 62. Note, that the tubing may, if necessary, be pulled off the anchor or drive portion 18 in order to properly seat the anchor. In any event, the tubing may be removed from the suture once it is threaded through the driver.

The essence of this invention is to provide a suture, attached to a suture anchor, with a suture stiffening or support structure to enable the suture to be fed through a cannulated suture anchor driver. The support structure minimizes the lateral flexibility of the suture and increases its column strength. While numerous variations may be feasible, two alternative embodiments of the invention are described below.

In FIG. 7a, a suture anchor is threaded with suture in the same manner as shown in FIG. 4a above. However, rather than inserting the entire length of suture into shrink tubing, the embodiment of FIG. 7 shows both ends of the suture beings inserted only a short distance (approximately 1 to 2 inches) into the shrink tubing 70 as shown in FIG. 7b. This may be done with a tool such as the aforementioned threader 34 or by using a simple conical flaring tool (not shown) to flare the end of the shrink tubing and thereby form a conical entryway into which the suture ends may be pushed. Heat is then applied to shrink the tubing to produce the anchor/suture/tubing assembly shown in FIG. 7c in which the majority of the shrink tubing does not frictionally engage any suture. However, because of the stiffness of the shrink tubing itself the entire assembly may be easily pushed or threaded through a cannulated driver as shown in FIG. 7d. The tubing may then be removed.

Figure 8A:
FIGS. 8a through 8c show the steps involved in producing a third embodiment of the invention.
Figure 8B:
Figure 8C:

In the embodiment of FIG. 8, the concept of providing a stiffening structure to the suture is presented in the form of an elongated rod 80. After the suture is threaded through the anchor as shown in FIG. 8a (a step identical to FIGS. 4a and 7a above), the proximal ends of the suture are inserted a short distance (approximately ½ inch) into the distal end of an elongated rod 80 (FIG. 8b). The rod may be hollow or solid and the suture may be swaged into the rod (FIG. 8c) or attached in some other way. Rod 80 is not shrinkable although its outside diameter must be small enough to fit within the bore of a cannulated driver.

Figure 9:
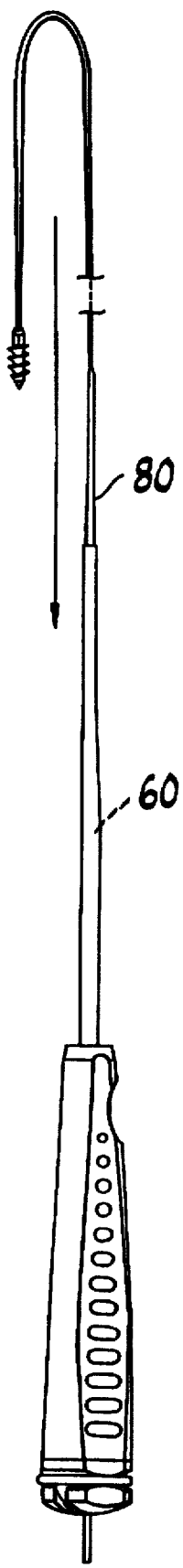
FIG. 9 shows the manner in which the third embodiment of the invention may be loaded into a cannulated driver.

As shown in FIG. 9, the anchor/suture/rod assembly of FIG. 8 may be easily threaded through a cannulated driver by holding the driver vertically and allowing gravity to feed rod 80 through bore 60 of the driver. The rod may then be removed.

It will be understood by those skilled in the art that numerous improvements and modifications may be made to the preferred embodiments of the invention disclosed herein without departing from the spirit and scope thereof.

What is claimed:

1. A pre-loaded suture anchor assembly for attachment to an anchor driver comprising:
   anchor body having a suture receiving means for receiving suture:
   a suture having predetermined length and having a first end and a second end, said suture received in said suture receiving means and extending therefrom;
   an elongated suture retaining means secured end-to-end to said first and second ends of said suture, and extending away therefrom, for holding said ends of said suture.

2. A pre-loaded suture anchor assembly according to claim 1 wherein said suture has two ends extending from said anchor and said suture retaining means comprises an elongated rod, having a proximal end and a distal end, said proximal end secured to the ends of said suture.

3. A pre-loaded suture anchor assembly for attachment to an anchor driver comprising:
   an anchor body having a suture receiving means for receiving suture;
   a suture having predetermined length and having a first end and a second end, said suture received in said suture receiving means and extending therefrom:
   a hollow, elongated substantially straight tubular sleeve means having an axial bore with open distal and proximal ends for holding both of said ends of said suture by frictionally engaging said ends within said axial bore of said sleeve means.

4. A pre-loaded suture anchor assembly according to claim 3 wherein said distal end of said sleeve means frictionally engages a predetermined portion of said anchor body.

5. A pre-loaded suture anchor assembly according to claim 3 wherein said distal end of said sleeve means comprises a heat-shrinkable tube.

6. A pre-loaded suture anchor assembly according to claim 3 wherein said suture receiving means comprises an eyelet member and wherein said eyelet member receives an intermediate portion of said suture such that a pair of suture portions are formed from said suture one suture portion extending between said anchor body and said first suture end and the other of said suture portions extending between said anchor body and said second suture end.

7. A pre-loaded suture anchor assembly according to claim 6 wherein said sleeve means frictionally engages both, said first and second ends of said suture.

8. A method of producing a pre-loaded suture anchor assembly for attachment to a suture anchor driver comprising the steps of:
   providing a suture anchor having a suture receiving means for receiving suture;
   providing a predetermined length of suture;
   engaging a predetermined length of suture with said suture receiving means so that at least one end of said suture extends from said suture anchor;
   providing a predetermined length of suture-supporting means for decreasing the lateral flexibility of an end portion of said suture to enable said suture to be engaged end-to-end with said driver;
   placing said at least one end of said suture into one end of said suture-supporting means;
   causing said suture-supporting means to frictionally engage said suture.

9. A method according to claim 8 wherein said suture receiving means is an eyelet and said step of engaging further comprises threading said at least one end of said suture through said eyelet.

10. A method according to claim 9 further comprising folding said suture upon itself to cause both ends of said suture to extend from said eyelet.

11. A method according to claim 8 wherein said suture-supporting means is shrinkable tubing and wherein the step of:

causing said suture-supporting means to frictionally engage said suture comprises shrinking said shrinkable tubing.

12. A method according to claim 8 wherein said suture-supporting means is an elongated rod having a proximal end and a distal end.

13. A method according to claim 8 further comprising the steps of:

providing a cannulated anchor driver having an axial bore and an anchor engaging means at its distal end for engaging said anchor in order to enable it to be driven at a predetermined work site;

inserting said suture supporting means into the axial bore of said cannulated anchor driver;

removing said suture supporting means.

14. A method according to claim 12 further comprising the steps of:

providing a cannulated anchor driver having an axial bore and an anchor engaging means at its distal end for engaging said anchor in order to enable it to be driven at a predetermined work site;

holding said driver in a vertical position to receive said elongated rod;

inserting said rod into said axial bore and allowing it to fall by gravity through said driver.

15. In combination, a suture anchor assembly comprising:

a suture anchor, a predetermined length of suture and a suture retaining means for supporting at least one end of said suture; and a cannulated driver for driving said suture anchor, said driver having an internal axial bore which has a predetermined diameter large enough to receive said suture retaining means therethrough.

16. A method of enabling a user to load a pre-loaded suture anchor assembly into a cannulated driver for driving a suture anchor comprising the steps of:

providing a pre-loaded suture anchor assembly comprising a suture anchor, a predetermined length of suture and suture support means secured to at least one end of said suture;

inserting said suture support means into and through the bore of said cannulated driver;

removing said suture support means.

\* \* \* \* \*